(12) United States Patent
Kim et al.

(10) Patent No.: US 12,029,770 B2
(45) Date of Patent: Jul. 9, 2024

(54) **COMPOSITION FOR ALLEVIATING FATIGUE OR ENHANCING EXERCISE CAPABILITY COMPRISING *ANGELICA GIGAS* EXTRACT, *CNIDIUM OFFICINALE* EXTRACT, AND *PAEONIA LACTIFLORA* EXTRACT**

(71) Applicant: KOLMAR BNH CO., LTD, Daejeon (KR)

(72) Inventors: Hyun Kyu Kim, Sejong (KR); Hak Sung Lee, Chungcheongbuk-do (KR); Seul Ki Kim, Sejong (KR); Da Ae Kwon, Seoul (KR); Young Sang Kim, Sejong (KR)

(73) Assignee: KOLMAR BNH CO., LTD (KR)

( * ) Notice: Subject to any disclaimer, the term of this patent is extended or adjusted under 35 U.S.C. 154(b) by 393 days.

(21) Appl. No.: 17/279,799

(22) PCT Filed: Sep. 24, 2019

(86) PCT No.: PCT/KR2019/012397
§ 371 (c)(1),
(2) Date: Mar. 25, 2021

(87) PCT Pub. No.: WO2020/067699
PCT Pub. Date: Apr. 2, 2020

(65) Prior Publication Data
US 2022/0023364 A1 Jan. 27, 2022

(30) Foreign Application Priority Data

Sep. 28, 2018 (KR) .................. 10-2018-0115851
Sep. 28, 2018 (KR) .................. 10-2019-0079535

(51) Int. Cl.
*A61K 36/00* (2006.01)
*A23L 33/105* (2016.01)
*A61K 36/232* (2006.01)
*A61K 36/234* (2006.01)
*A61K 36/65* (2006.01)

(52) U.S. Cl.
CPC .......... *A61K 36/232* (2013.01); *A23L 33/105* (2016.08); *A61K 36/234* (2013.01); *A61K 36/65* (2013.01); *A61K 2236/333* (2013.01)

(58) Field of Classification Search
CPC .............................. A61K 36/65; A61K 36/234
See application file for complete search history.

(56) References Cited

U.S. PATENT DOCUMENTS 6,964,785 B2    11/2005    Jo et al.

FOREIGN PATENT DOCUMENTS

| EP | 3360561 A1 * | 8/2018 | ............. A23L 33/10 |
|---|---|---|---|
| KR | 10-2000-0066777 A | 11/2000 | |
| KR | 2003037929 A * | 5/2003 | ............... A23F 3/12 |
| KR | 10-2004-0087711 A | 10/2004 | |
| KR | 10-2005-0053046 A | 6/2005 | |
| KR | 10-2009-0104196 A | 6/2009 | |
| KR | 10-2011-0056904 A | 5/2011 | |
| KR | 2016-0076014 A | 6/2016 | |
| KR | 10-2018-0016275 A | 2/2018 | |
| KR | 10-1873025 B1 | 7/2018 | |
| WO | WO 2009/069921 A2 | 6/2009 | |

OTHER PUBLICATIONS

Choi et al., "Vascular Protective Role of Samul-Tang in HUVECs: Involvement of Nrf2/HO-1 and NO", *Evidence-Based Complementary and Alternative Medicine* 2016:1-14, https://doi.10.1155/2016/9580234, Jan. 2016.
Extended European Search Report for EP Application No. 19866393.2 dated Aug. 10, 2022, 11 pages.
Park et al., "Protective Effects of HemoHIM on Immune and Hematopoietic Systems Against γ-Irradiation", *Phytotherapy Research* 28(2):245-251, https://doi.10.1002/ptr.4982, 2014.
Shin et al., "Decrease of immobility behavior in forced-swimming test and immune system enhancing effect of traditional medicine Gamisipjundaebo-tang", *Pharmacology, Biochemistry and Behavior* 79(2):253-259, https://doi.10.1016/j.pbb.2004.07.006, Oct. 2004.
Kim et al., "Effects of A Constituent Herbs of Samul-tang on Anti-fatigue", 1998, Thesis, Kyung Hee University, 1-58.
Kim et al., "Effects of A Constituent Herbs of Samul-tang on Anti-fatigue", 2000, The Journal of Oriental Gynecology vol. 13, No. 1, 54-93.
Xu et al., "β-glucan Salecan Improves Exercise Performance and Displays Anti-Fatigue Effects through Regulating Energy Metabolism and Oxidative Stress in Mice", Nutrients, 2018, 10, 858, 13 pages.
Bae et al. "Effects of Samul-tang and Constituent Herbs on a Contracted Artery of Rabbit", 2000, Korean J. Orient. Int. Med., 21(1), pp. 23-30.
Lee et al., "Hemopoietic effect of extracts from constituent herbal medicines of Samul-tang on phenylhydrazine-induced hemolytic anemia in rats", 2014, Int J Clin Exp Pathol, 7(9), pp. 6179-6185.

(Continued)

*Primary Examiner* — Qiuwen Mi
(74) *Attorney, Agent, or Firm* — LATHROP GPM LLP; Brian C. Trinque

(57) ABSTRACT

Provided is a composition for alleviating fatigue or enhancing exercise capability including extracts or fractions of *Angelica gigas, Cnidium officinale*, and *Paeonia lactiflora* as active ingredients. The composition including the extracts or fractions of *Angelica gigas, Cnidium officinale*, and *Paeonia lactiflora* as active ingredients may effectively alleviate fatigue accumulated in the body and enhance exercise capability by multilaterally controlling various factors involved in physical fatigue and/or enhancement of exercise capability. Specifically, the composition may effectively control the factors related to fatigue by increasing the expression level of HO-1 by activating the Nrf-2 pathway. Also, since extracts of natural plants or fractions thereof are used as active ingredients, the composition is completely harmless to the human body and may be used safely.

6 Claims, 8 Drawing Sheets
Specification includes a Sequence Listing.

(56) References Cited

OTHER PUBLICATIONS

Um et al., "Antioxidant, Anti-Wrinkle Activity and Whitening Effect of Fermented Mixture Extracts of *Angelica gigas, Paeonia Lactiflora, Rehmannia chinensis* and *Cnidium officinale*", 2017, Korean J. Medicinal Crop Sci., 25(3), pp. 152-159.

* cited by examiner

[FIG. 1A]
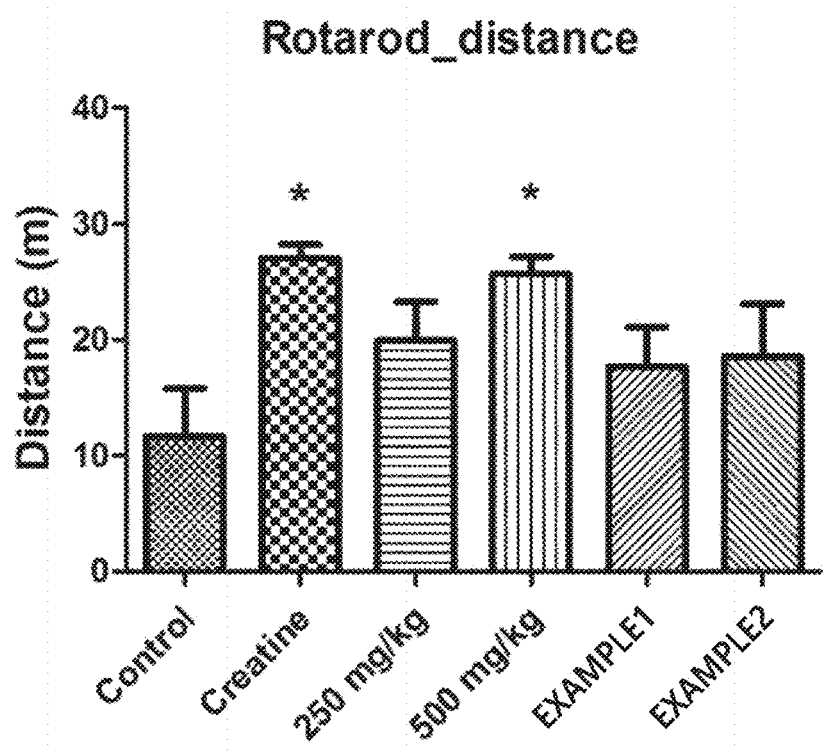
[FIG. 1B]
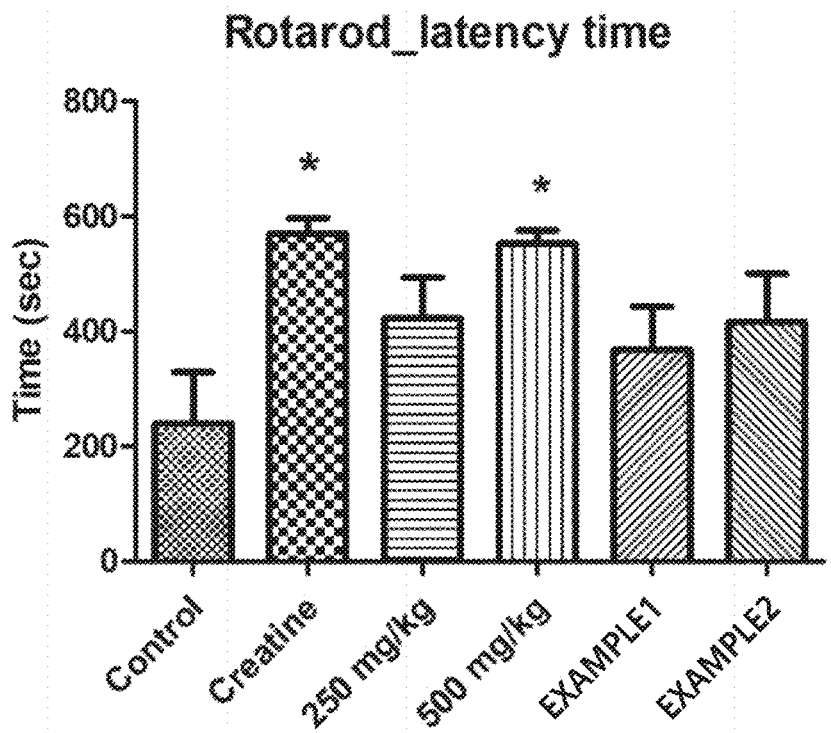

[FIG. 2]
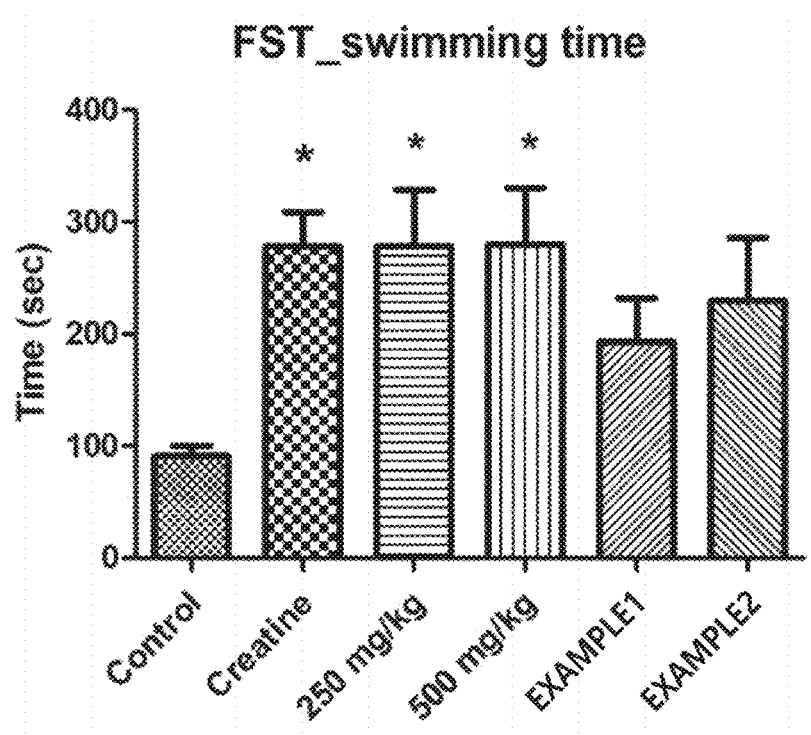
[FIG. 3]
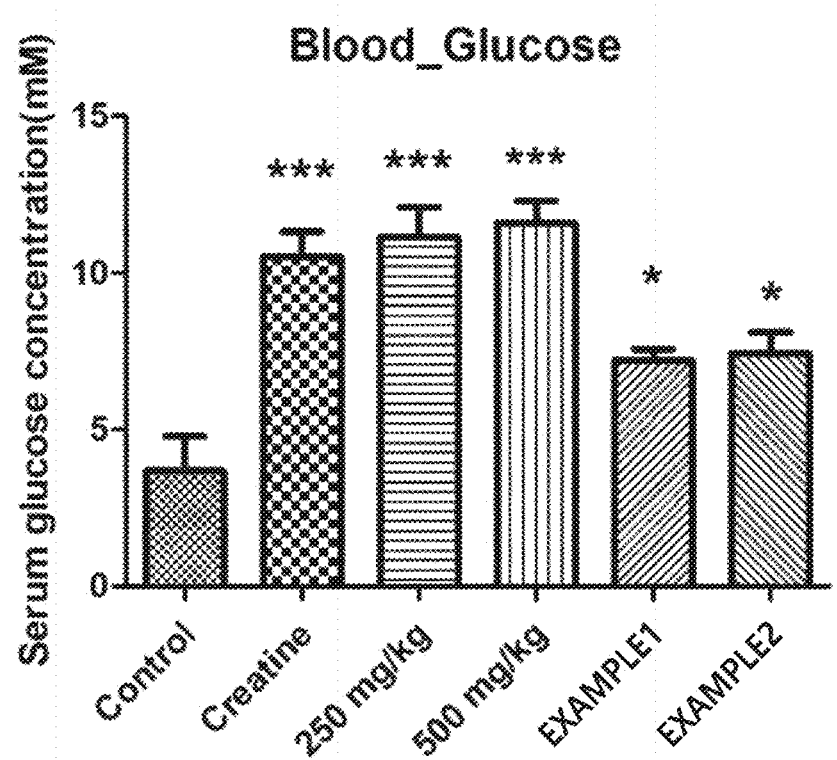

[FIG. 4A]
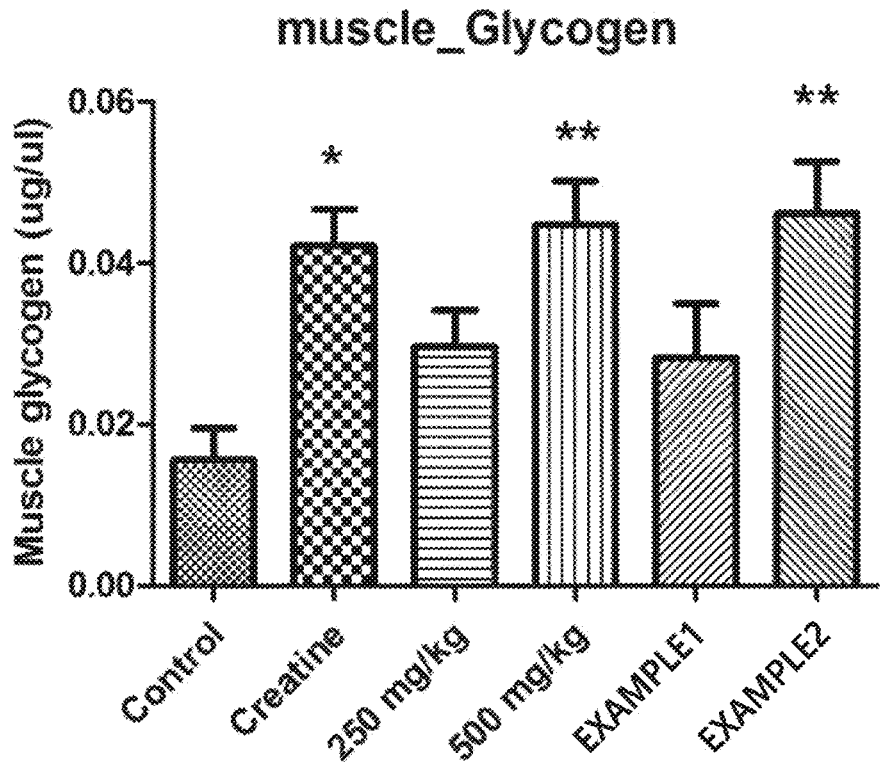
[FIG. 4B]
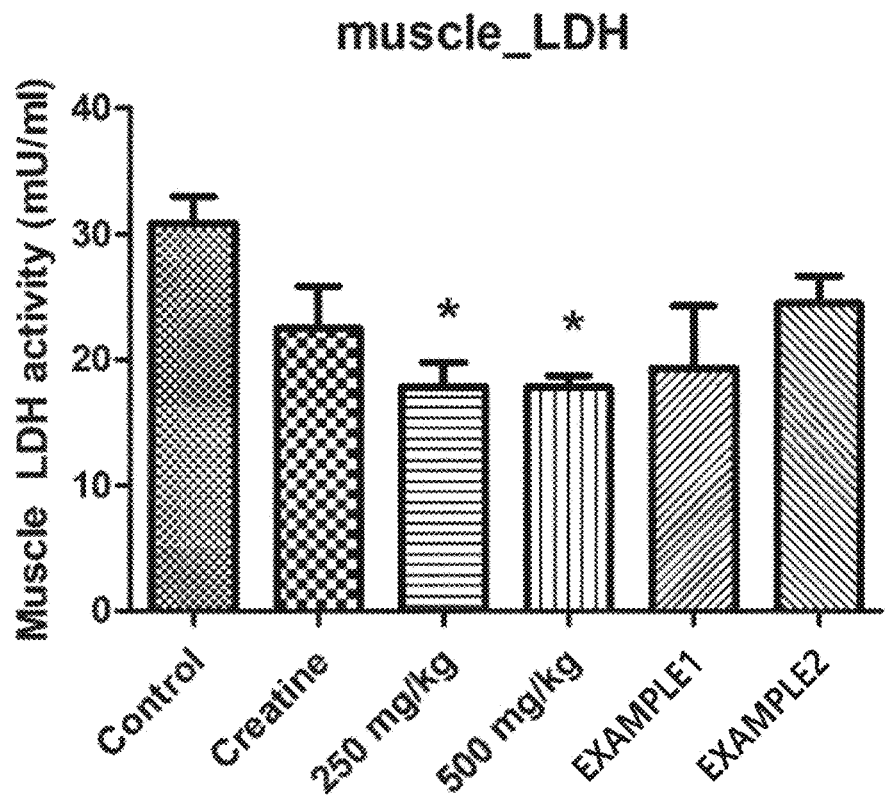

[FIG. 5A]
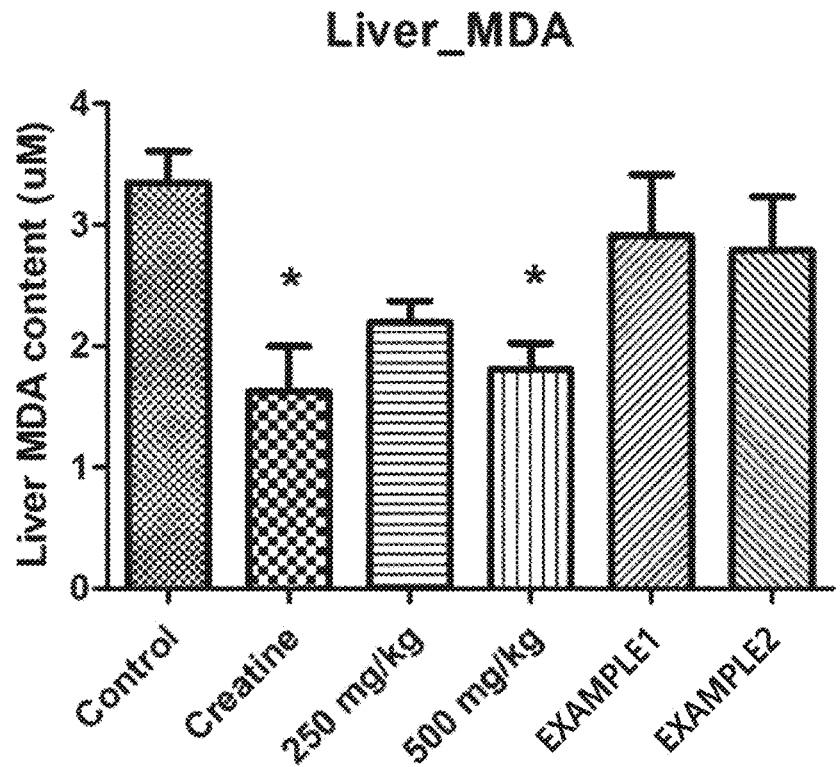
[FIG. 5B]
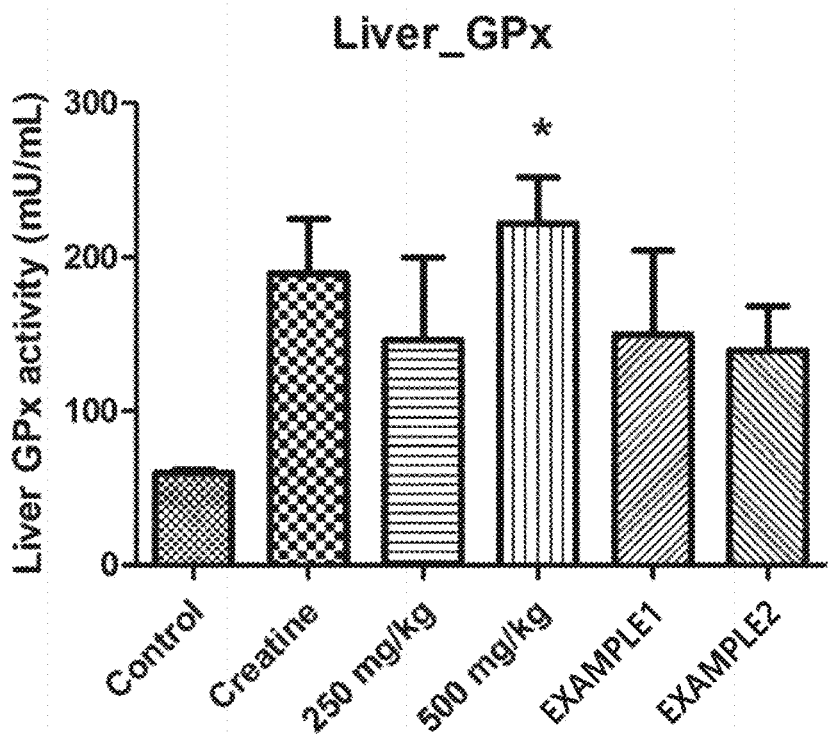

[FG. 6A]
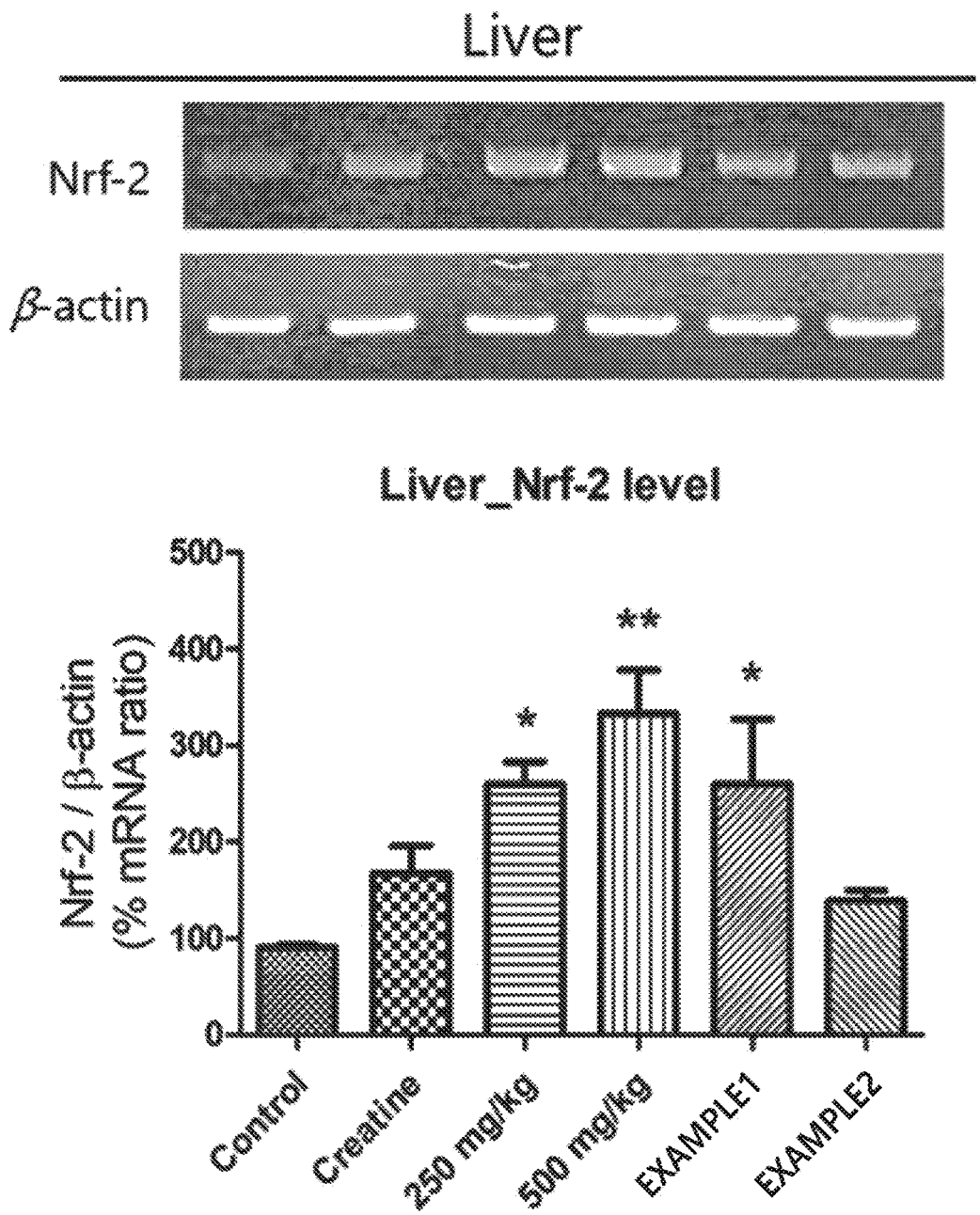

[FIG. 6B]
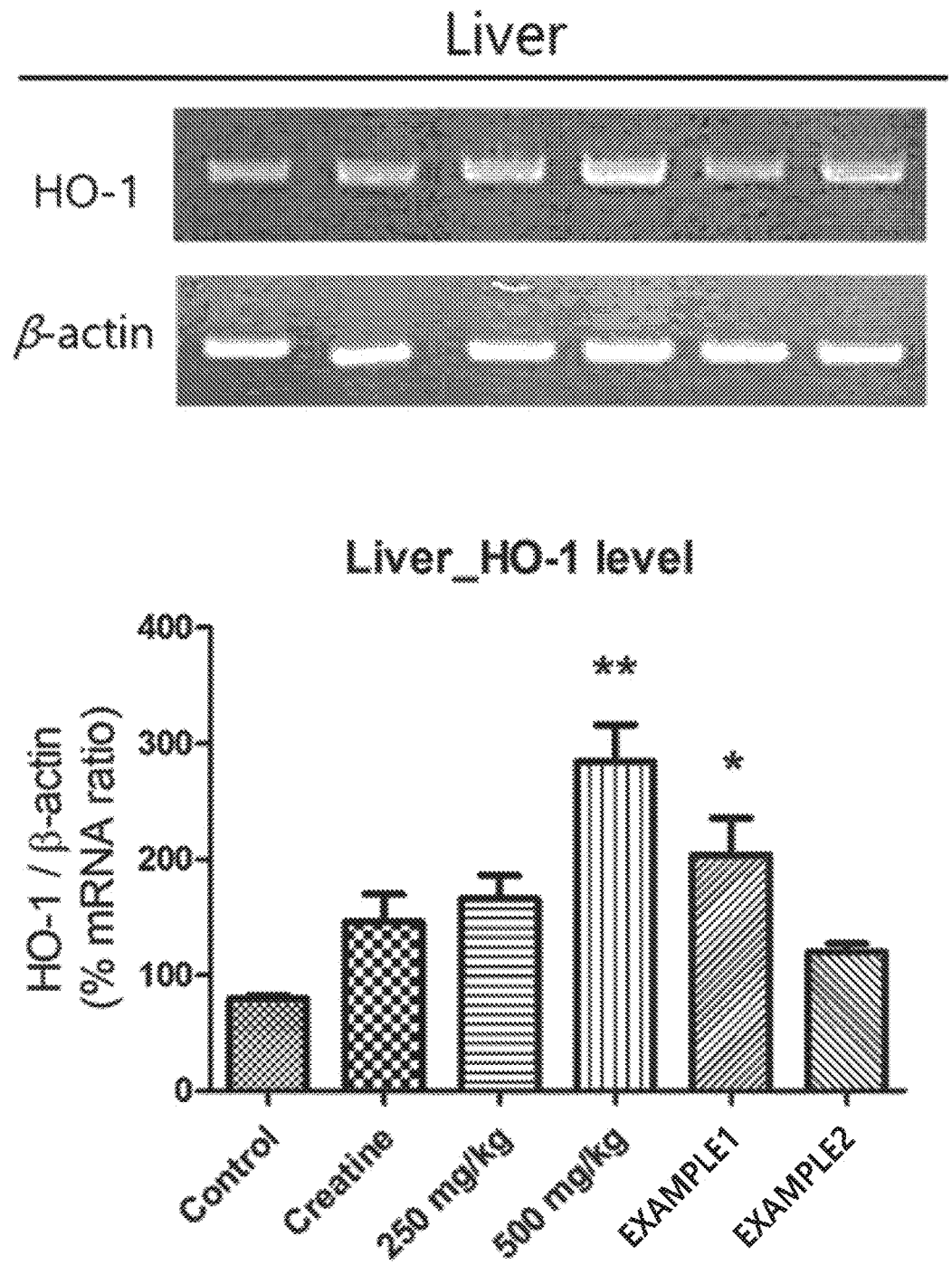

[FIG. 7A]
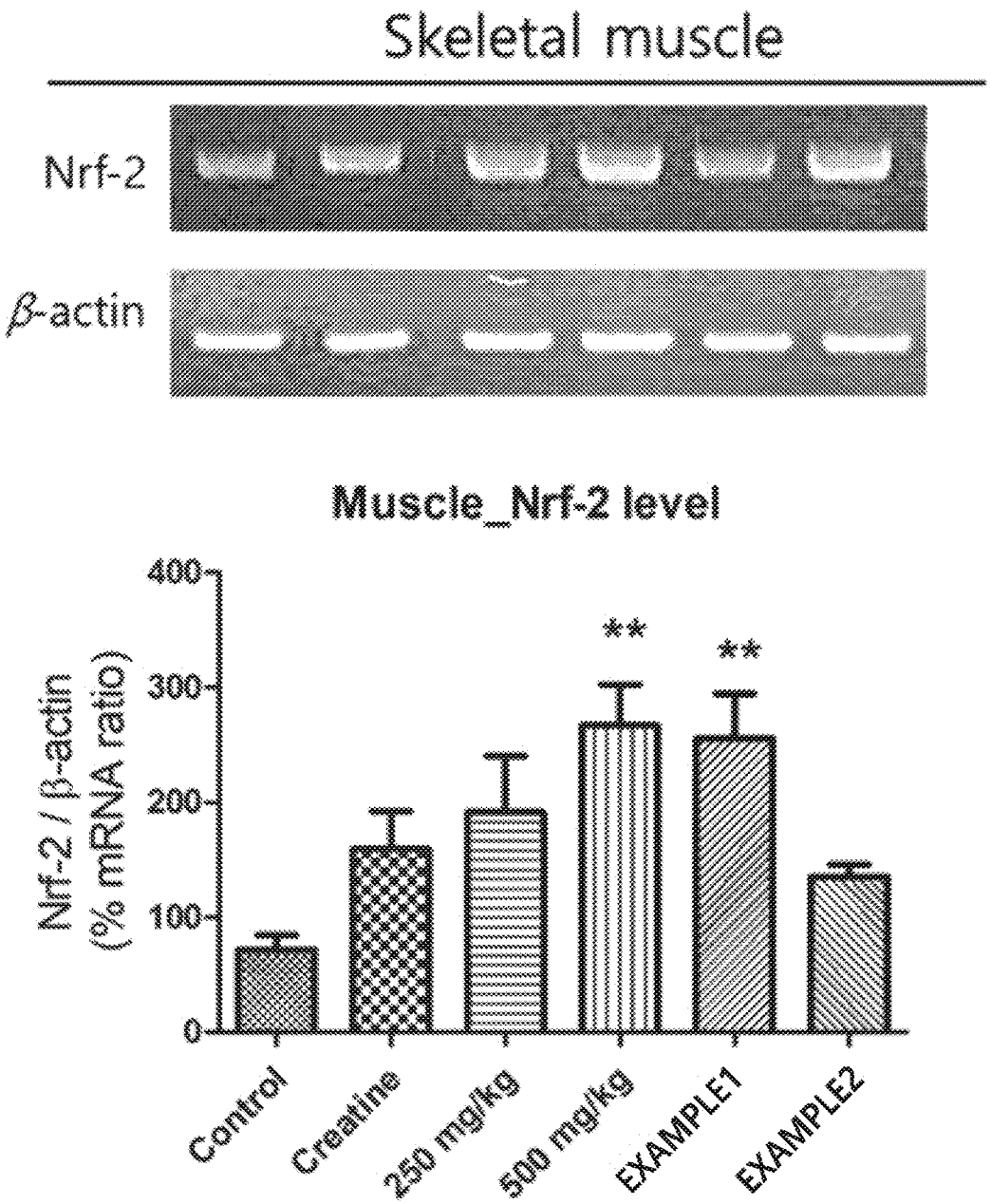

[FIG. 7B]
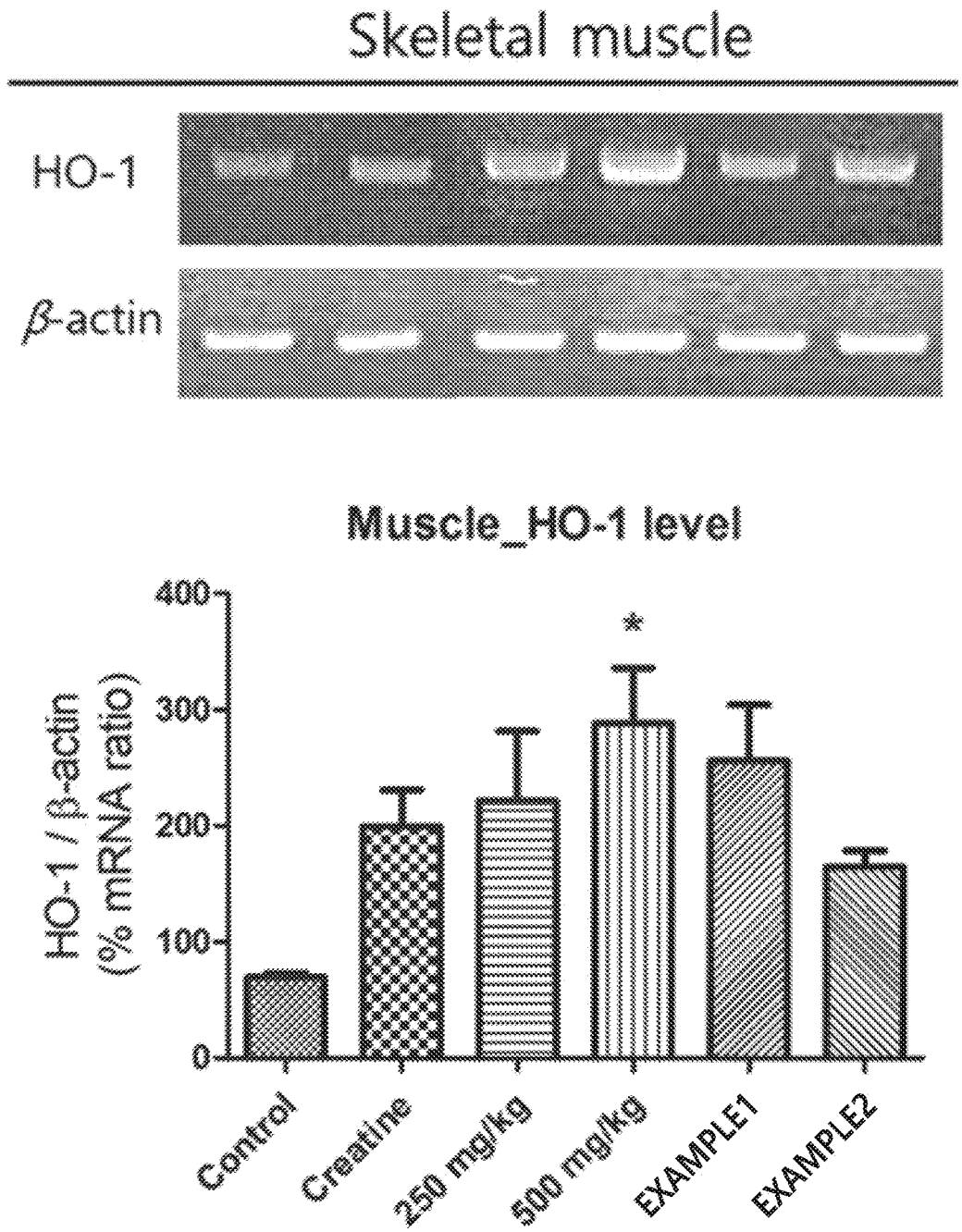

COMPOSITION FOR ALLEVIATING FATIGUE OR ENHANCING EXERCISE CAPABILITY COMPRISING *ANGELICA GIGAS* EXTRACT, *CNIDIUM OFFICINALE* EXTRACT, AND *PAEONIA LACTIFLORA* EXTRACT

SEQUENCE LISTING

The instant application contains a Sequence Listing which has been submitted electronically in ASCII format and is hereby incorporated by reference in its entirety. Said ASCII copy, created on Sep. 27, 2021, is named 719556HNT-045US_ST25.txt and is 1,691 bytes in size.

TECHNICAL FIELD

The present invention relates to a composition for alleviating fatigue or enhancing exercise capability including extracts or fractions of *Angelica gigas, Cnidium officinale,* and *Paeonia lactiflora* as active ingredients.

BACKGROUND ART

Fatigue is broadly classified into mental fatigue and physical fatigue. In general, physical fatigue is defined as a state in which a force required for muscle contraction is not sufficiently exerted or maintained; a state in which physical or mental capacity has declined, due to overwork or energy exhaustion, to the extent that the fatigue cannot be improved by rest; or a state in which working efficiency or exercise capability have declined. Symptoms of fatigue have been known to include tiredness, weariness, exhaustion, drowsiness, difficulty concentrating, headache, muscle pain, and the like.

Lack of or inability to use an energy source stored in the body, accumulation of fatigue substances such as reactive oxygen species by metabolism, and loss of homeostasis in the body have been known as general causes of physical fatigue. In particular, it has been found that the reactive oxygen species are generated by metabolism, and generation thereof is increased by excessive physical activities and excessive mental/physical stress. Meanwhile, fatigue is often caused by a combination of various factors, not by only a single factor.

Although it is required to supply sufficient energy, rest, inhibit generation of fatigue substances in the body, remove the fatigue substances, or the like in order to alleviate physical fatigue, in fact, it is difficult to realize sufficient nutrient intake and rest in the busy, modern society of today. Thus, there is a need to develop substances capable of alleviating or inhibiting fatigue.

Meanwhile, with increased reluctance on the part of consumers toward chemically synthesized drugs in recent years, there is an increasing need to develop herbal medicines using natural substances. Therefore, research into anti-fatigue compositions using extracts of natural objects has been conducted, but substances capable of rapidly and effectively alleviating fatigue have not yet been developed.

DISCLOSURE

Technical Problem

An object of the present invention is to provide a composition having excellent effects on fatigue alleviation or exercise capability enhancement.

Another object of the present invention is to effectively alleviate physical fatigue and enhance exercise capability without side effects.

Technical Solution

An aspect of the present invention provides a composition for alleviating fatigue and enhancing exercise capability including extracts or fractions of *Angelica gigas, Paeonia lactiflora,* and *Cnidium officinale* as active ingredients.

Another aspect of the present invention provides use of extracts or fractions of *Angelica gigas, Paeonia lactiflora,* and *Cnidium officinale* for alleviating fatigue and enhancing exercise capability in preparation of foods.

Advantageous Effects

A composition including extracts or fractions of *Angelica gigas, Paeonia lactiflora,* and *Cnidium officinale* as active ingredients according to an embodiment of the present invention may effectively alleviate fatigue accumulated in the body by multilaterally controlling various factors involved in alleviation of physical fatigue and enhancement of exercise capability. Specifically, the composition may effectively control the factors related to fatigue alleviation and/or exercise capability enhancement by increasing the expression level of HO-1 by activating the Nrf-2 pathway. In addition, since extracts or fractions of plants, as natural objects, are contained in the composition as active ingredients, the composition is harmless to the human body and may be used safely.

BRIEF DESCRIPTION OF DRAWINGS

FIG. 1 shows distance (FIG. 1A) and exercise time (FIG. 1B) in a rotarod test according to treatment with the composition of the present invention.

FIG. 2 shows time until exhaustion in a forced swimming test according to treatment with the composition of the present invention.

FIG. 3 shows changes in blood glucose concentration after a behavioral test according to treatment with the composition of the present invention.

FIG. 4 shows changes in activity and concentration of glycogen (FIG. 4A), and LDH (FIG. 4B) in muscle tissue after a behavioral test according to treatment with the composition of the present invention.

FIG. 5 shows changes in activity and concentration of MDA (FIG. 5A) and GPx (FIG. 5B) in liver tissue after a behavioral test according to treatment with the composition of the present invention.

FIG. 6 shows RT-PCR test results indicating expression of Nrf-2 (FIG. 6A) and HO-1 (FIG. 6B) genes in liver tissue after a behavioral test according to treatment with the composition of the present invention.

FIG. 7 shows RT-PCR test results including expression of Nrf-2 (FIG. 7A) and HO-1 (FIG. 7B) genes in muscle tissue after a behavioral test according to treatment with the composition of the present invention.

In FIGS. 1 to 7, 250 mg/kg and 500 mg/kg refer to administered doses of Example 3.

BEST MODE

The present invention will be described in detail.

In an aspect, the present invention provides a composition for alleviating fatigue or enhancing exercise capability including extracts or fractions of *Angelica gigas, Paeonia lactiflora*, and *Cnidium officinale* as active ingredients.

Also, in another aspect, the present invention provides a use of extracts or fractions of *Angelica gigas, Paeonia lactiflora*, and *Cnidium officinale* for alleviating fatigue and enhancing exercise capability in preparation of foods.

In this aspect, the fatigue may include muscle fatigue.

*Angelica gigas* is a perennial aromatic plant belonging to the Apiaceae family and is distributed in Korea, China, and Japan. *Angelica gigas* Nakai, *Angelica sinensis* (Oliv.) Diels, and *Angelica acutiloba* have been known, and *Angelica gigas* Nakai has been widely used for controlling blood pressure and treating anemia due to excellent blood-nourishing action, blood circulation action, and the like.

*Cnidium officinale* is a perennial aromatic plant in the Apiaceae family and is distributed in Korea and Japan. Since ancient times, roots of *Cnidium officinale* have been used as soothing, analgesic, and tonic agents.

Throughout the specification, the *Paeonia* may refer to a plant belonging the genus *Paeonia*, and plants belonging to the genus *Paeonia* may include at least one selected from the group consisting of *Paeonia lactiflora, Paeonia japonica* Miyabe & Takeda, *Paeonia lactiflora* Pall., *Paeonia lactiflora* Pall. var. *hirta* Regel, and *Paeonia lactiflora* Pall. var. *trichocarpa* (Bunge) Stem, without being limited thereto.

Plants belonging to the genus *Paeonia* are dicotyledonous perennial plants in the family Paeoniaceae and have been used as therapeutic agents for relieving pain, e.g., abdominal pain and menstrual pain, and treating amenorrhoea, hemoptysis, anemia, bruises, and the like.

In an aspect, the extracts or fractions of *Angelica gigas, Paeonia lactiflora*, and *Paeonia lactiflora* may include extracts or fractions of fruits, stems, leaves, or underground parts of the respective plants, and also extracts or fractions of the whole plants, but may preferably include extracts or fractions of roots of the plants.

Throughout the specification, the "extract" includes all substances prepared by obtaining components of natural objects from the inside regardless of methods for extractions or types of components. For example, the extract may refer to components of natural objects soluble in a solvent such as water or an organic solvent obtained from natural objects using the solvent.

The extract, as a mixed extract including all of *Angelica gigas, Cnidium officinale*, and *Paeonia lactiflora*, may be an extract obtained from a mixture of the three substances or a mixture of individually obtained extracts of the three substances, and may also be any mixed extracts thereof obtained using methods well known in the art, without limitation.

The extracts or fractions of the extracts may be used as-is, but may be used in the form of a concentrated extract after filtration and concentration or a freeze-dried product after concentration and freeze-drying.

In an embodiment, the *Angelica gigas, Paeonia lactiflora*, and *Cnidium officinale* may be contained in a weight ratio of (1 to 100):(1 to 100):(1 to 100). The weight ratio of the extracts or fractions of *Angelica gigas, Paeonia lactiflora*, and *Cnidium officinale* may be in the range of (1 to 30):(1 to 30):(1 to 30), preferably in the range of (1 to 10):(1 to 10):(1 to 10), more preferably in the range of (1 to 5):(1 to 5):(1 to 5), and even more preferably in the range of (0.8 to 1.2):(0.8 to 1.2):(0.8 to 1.2), and the weight ratio may be 1:1:1 according to an embodiment.

Since a combination of the extracts or fractions of these plants is used, the composition may have remarkably superior effects when compared to a case using an extract or fraction of only one of the plants.

Also, the composition may have remarkably superior effects on fatigue alleviation or exercise capability enhancement compared to those including extracts or fractions of plants other than *Angelica gigas, Paeonia lactiflora*, and *Cnidium officinale*.

According to an embodiment, the extracts or fractions of *Angelica gigas, Paeonia lactiflora*, and *Cnidium officinale* may be contained in an amount of 0.0001 wt % to 90 wt % based on a total weight of the composition. Preferably, the extracts or fractions may be contained in the composition in an amount of 30 wt % to 80 wt %, more preferably 35 wt % to 70 wt %, even more preferably 40 wt % to 65 wt %, based on the total weight of the composition.

In an aspect, the composition may activate the nuclear factor erythroid 2-related factor-2 (Nrf-2) pathway.

Also, the composition may increase an expression level of heme oxygenase-1 (HO-1).

In this aspect, an extraction solvent to obtain the extracts may include water, an organic solvent, or an aqueous solution of the organic solvent.

When the extraction solvent is water, the extracts may include extracts obtained by way of cold water or hot water.

The organic solvent is not particularly limited but may be a $C_1$-$C_5$ lower alcohol such as methanol, ethanol, isopropyl alcohol, n-propyl alcohol, n-butanol, and isobutanol, a polyhydric alcohol such as glycerol, ethylene glycol, propylene glycol, and 1,3-butylene glycol, a hydrocarbon-based solvent such as methyl acetate, ethyl acetate, benzene, n-hexane, diethyl ether, dichloromethane, and chloroform, or a non-polar organic solvent such as petroleum ether, methyl acetate, benzene, hexane, chloroform, methylene chloride, dimethyl ether, and ethyl acetate.

A concentration of the aqueous solution of the organic solvent may be in the range of 1% (v/v) to 99% (v/v), specifically in the range of 60% (v/v) to 98% (v/v), more specifically in the range of 80% (v/v) to 95% (v/v), and even more specifically 95% (v/v).

In an embodiment, the fractions may include polysaccharide fractions.

In an embodiment, the composition may include a mixture of the extracts and the fractions.

When the composition is a mixture of extracts and fractions, a weight ratio of the extracts to the fractions may be in the range of about (40 to 80):(20 to 60), preferably in the range of (45 to 75):(25 to 55), more preferably in the range of (50 to 70):(30 to 50), even more preferably in the range of (65 to 70):(30 to 35), and most preferably 65:35, without being limited thereto.

Also, in this aspect, an amount of the fractions may be in the range of 10 wt % to 60 wt %, preferably in the range of 20 wt % to 50 wt %, more preferably in the range of 25 wt % to 45 wt %, and even more preferably 30 wt % to 40 wt %, based on a total amount of the extracts and fractions.

In an aspect, the composition may effectively alleviate physical fatigue and/or enhance exercise capability by controlling various factors involved in fatigue and exercise capability.

In an aspect, the composition may be a food composition for alleviating fatigue or enhancing exercise capability including extracts of *Angelica gigas, Paeonia lactiflora*, and *Cnidium officinale* and polysaccharide fractions thereof as active ingredients, wherein a weight ratio of the extracts and the polysaccharide fractions is in the range of (60 to 70):(30 to 40). The composition may be a food composition for alleviating fatigue or enhancing exercise capability including one or more of the following characteristics: i) increase in glucose level; ii) increase in glycogen concentration; iii)

decrease in lactate dehydrogenase (LDH) concentration; iv) decrease in malondialdehyde (MDA) concentration; v) increase in glutathione peroxidase (GPx) concentration; vi) increase in expression of nuclear factor erythroid 2-related factor-2 (Nrf-2); and vii) increase in expression of heme oxygenase-1 (HO-1).

For example, the composition may increase distance and exercise time as a result of a behavior test. Also, the composition may increase the blood glucose level, and may increase the concentration of glycogen and decrease the concentration of lactate dehydrogenase (LDH) in the muscles. Also, the composition may decrease the concentration of malondialdehyde (MDA) and increase the concentration of GSH-Px in the liver. Also, the composition may increase the concentration of nuclear factor erythroid 2-related factor-2 (Nrf-2) and the expression level of heme oxygenase-1 (HO-1) in the liver and muscles.

Specifically, the composition may alleviate fatigue via an antioxidant reaction by inhibiting reactive oxygen species by promoting HO-1 activity by activating the Nrf-2 pathway, decreasing MDA and LDH, and increasing the activity of GPx.

HO-1 is known as a representative cellular defensive phase 2 detoxifying antioxidant enzyme, and induction of HO-1 acts as an important mechanism for various diseases or conditions related to oxidative stress or inflammatory damage to tissue. In addition, Nrf-2, as a very important transcription factor in protecting cells against oxidative stress and carcinogenesis, activates transcription of antioxidant enzymes and phase 2 detoxifying enzymes (Nutrients 2018, 10, 858).

In an aspect, the composition may be a food composition.

The food composition may include a health functional food composition, and the health functional food composition may be various foods, beverages, gums, teas, vitamin complexes, and health supplements in the form of powders, granules, tablets, capsules, or drinks.

The food composition in each formulation may further include other components commonly used in the art, which are appropriately selected and blended in accordance with the formulation or purpose of use by those skilled in the art without any particular difficulty, in addition to the active ingredients, and synergistic effects may be obtained by using the active ingredients in combination with other raw materials.

In an embodiment, the composition may include other components capable of providing synergistic effects on the main effects of the present invention within a range not to impair the main effects of the present invention. For example, the composition may further include an additive for improvement of physical properties such as a fragrance, a pigment, a sterilizer, an antioxidant, a preservative, a humectant, a thickener, an inorganic salt, an emulsifier, and a synthetic polymer material.

In addition, the composition may further include an auxiliary component such as a water-soluble vitamin, an oil-soluble vitamin, a polymer peptide, a high-molecular-weight polysaccharide, and a seaweed extract. These components may be appropriately selected and blended in accordance with the formulation or purpose of use by those skilled in the art without any particular difficulty, and the amounts thereof may be selected within a range not to impair the objects and effects of the present invention. For example, the amounts of the components may be in the range of 0.01 wt % to 5 wt %, more specifically in the range of 0.01 wt % to 3 wt %, based on the total weight of the composition.

MODE FOR INVENTION

Hereinafter, the present invention will be described in more detail with reference to the following examples. However, the following examples are merely presented to exemplify the present invention, and the scope of the present invention is not limited thereto and would be obvious to those skilled in the art.

[Preparation Example] Preparation of Composition

[Preparation Example 1-1] Preparation of Extract

*Angelica gigas* roots, *Cnidium rhizomes*, and *Paeonia lactiflora* roots were each dried in the shade and shredded, and the shredded medical plants were mixed in the same weight ratio. Distilled water was added to the mixture such that the weight of the distilled water was 10 times the total weight of the medical plants (1000 mL of distilled water per 100 g of the medical plants), followed by hot water extraction for 4 hours. Solids were removed from the extract, and the resultant was concentrated under reduced pressure to obtain an extract (Example 1).

[Preparation Example 1-2] Preparation of Polysaccharide Fraction

After taking a part of the extract prepared in Preparation Example 1-1, 95% ethanol 4 times the volume of the extract was added thereto and maintained at a temperature below 25° C. for 16 hours. The resultant was subjected to centrifugation, and precipitated crude polysaccharide fractions (Example 2) were collected and used.

[Preparation Example 1-3] Preparation of Composition

The extract prepared in Preparation Example 1-1 (Example 1) and the crude polysaccharide fractions prepared in Preparation Example 1-2 (Example 2) were mixed in a weight ratio of about (65 to 70):(30 to 35) to prepare a mixture (Example 3).

Experimental Example

Using experimental mice, a rotarod test and a forced swimming test (FST) were performed.

6-week-old ICR mice (male) were used as the experimental mice. After acclimatization in a germ-free breeding device for one week, the mice were used in the experiment.

[Experimental Example 1] Rotarod Test

After carrying out pre-training twice during the acclimatization period, the rotarod test was performed for 3 weeks from the first day after the acclimatization period while administering samples (Examples 1 to 3 and creatine for positive control). The pre-training was carried out by increasing the speed from 4 rpm to 40 rpm.

The rotarod test was performed once per week immediately after the samples were administered and at 30 minutes after the samples were administered to measure latency time and distance. In this test, fall latency and distance were measured by accelerating the rotarod cylinder at a speed from 4 rpm to 40 rpm within 10 minutes, and an average value was obtained by repeating this process three times.

As a result, it was confirmed that distance and exercise time were increased in the examples when compared with the control, and exercise capability and endurance were also improved (FIG. 1). In particular, among the examples, remarkably superior effects were confirmed in Example 3, in which the mixture of the extracts and the fractions was used.

[Experimental Example 2] Forced Swimming Test (FST)

Forced swimming tests (*to measure time until exhaustion) were performed once a week immediately after the samples were administered, at 30 minutes after the samples were administered, and on the day of autopsy. A temperature of water in which swimming was conducted was 25° C.±5° C., the test was conducted by hanging a weight of 5% of the body weight on the mice, and an average value was obtained by repeating this process three times.

After FST, time until exhaustion and changes in concentrations of fatigue-related factors were measured. Specifically, on the day of autopsy, the rotarod test was performed and the FST conducted, and then autopsy was performed immediately thereafter. Blood, liver, and gastrocnemius of the hind legs were collected.

* A time at which the nose of each mouse sinks below the water surface for 5 seconds or more is determined as a point of exhaustion.

[Experimental Example 3] Measurement of Factors Related to Fatigue Alleviation/Exercise Capability Enhancement After separating serum from blood collected from the heart, a blood glucose level in the serum was measured, concentrations of glycogen and lactate dehydrogenase (LDH) in the muscles were measured, and concentrations of malondialdehyde (MDA) and glutathione peroxidase (GSH-Px) in the liver were measured.

[Experimental Example 4] RNA Extraction and Semi-Quantitative RT-PCR

Total RNA was extracted using an RNeasy Mini Kit (Qiagen, Hilden, Germany), and RNA was quantified using a NanoDrop 2000 UV-Vis spectrophotometer (Thermo Fisher Scientific Inc., Waltham, MA, USA). The extracted total RNA was reverse-transcribed using high-capacity cDNA reverse transcription kits (Applied Biosystems, Carlsbad, CA, USA) to synthesize cDNA. The synthesized cDNA was amplified using an AccuPower PCR Premix (Bioneer, Daejeon, Korea), and polymerase chain reaction was conducted using primers capable of specifically amplifying Nrf-2 and HO-1 genes (Nrf-2: Forward (5'→3'): TTCCTCTGCTGCCATTAGTCAGTC, Reverse (5'→3'): GCTCTTCCATTTCCGAGTCACTG, HO-1: Forward (5'→3'): CTGGAAGAGGAGATAGAGCGAA, Reverse (5'→3'): TCTTAGCCTCTTCTGTCACCCT, and-actin: Forward (5'→3'): GCCATGTACGTAGCCATCCA, Reverse (5'→3'): GAACCGCTCATTGCCGATAG).

The amplified cDNA was subjected to electrophoresis in a 1.8% agarose gel and stained with ethidium bromide (EtBr), and then expression levels of the target mRNA were quantified with Image J Software (NIH, Framingham, MA, USA) using-actin as a control and compared and analyzed. Expression levels of Nrf-2 and HO-1 genes related to antioxidation in tissue of the liver and muscles were measured using RT-PCR.

As a result, it was confirmed that distance and time until exhaustion increased during the exercise due to enhanced exercise capability (FIGS. 1 and 2), and fatigue-related factors were also improved in the case of samples administered according to the examples. Specifically, it was confirmed that the blood glucose level was significantly increased in the case of samples administered according to the examples when compared to the control (FIG. 3). As a result of analysis in the muscles, it was confirmed that the concentration of glycogen tends to increase and the concentration of LDH tends to significantly decrease (FIGS. 4A and 4B). It was also confirmed that the MDA content in the liver tends to significantly decrease (FIG. 5A) and the GPx content in the liver tends to significantly increase (FIG. 5B) compared to the control.

In addition, as a result of identifying the related factors, Nrf-2 and HO-1, by RT-PCR, the concentrations thereof significantly increase in both the liver and the muscle in the group administered with 500 mg/kg, thereby confirming that fatigue was alleviated thereby (FIGS. 6 and 7).

In this experiment, it was confirmed that the concentrations of HO-1 and Nrf-2 were increased by administering the compositions according to the examples. Based on the results of other antioxidant-related factors, it was confirmed that the extracts activated the Nrf-2 to promote expression of HO-1, thereby affecting results of MDA and GPx, which are antioxidant-related factors.

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:

1. A method for alleviating fatigue or enhancing exercise capability in a subject, comprising administering to the subject a composition consisting of water extracts and ethanol polysaccharide fractions of *Angelica gigas, Cnidium officinale*, and *Paeonia lactiflora* as active ingredients, wherein a weight ratio of the extracts or fractions of *Angelica gigas, Paeonia lactiflora*, and *Cnidium officinale* is 1:1:1, and wherein a ratio of water extract and ethanol polysaccharide fraction is 65:35.

2. The method of claim 1, wherein the fatigue comprises muscle fatigue.

3. The method of claim 1, wherein the composition activates a nuclear factor erythroid 2-related factor-2 (Nrf-2) pathway.

4. The method of claim 1, wherein the composition increases an expression level of heme oxygenase-1 (HO-1).

5. The method of claim 1, wherein the polysaccharide fraction is produced by extracting an aqueous extract with 95% ethanol.

6. The method of claim 1, wherein the composition is a food composition.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
```

```
ttcctctgct gccattagtc agtc                                               24

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
gctcttccat ttccgagtca ctg                                                23

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
ctggaagagg agatagagcg aa                                                 22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
tcttagcctc ttctgtcacc ct                                                 22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
gccatgtacg tagccatcca                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
gaaccgctca ttgccgatag                                                    20
```